(12) United States Patent
Chan et al.

(10) Patent No.: US 7,494,780 B2
(45) Date of Patent: Feb. 24, 2009

(54) EPIDIDYMIS-SPECIFIC DEFENSIN FOR EVALUATING AND REGULATING MALE FERTILITY

(75) Inventors: Hsiao Chang Chan, Shatin (HK); Chenxi Zhou, Guangdon (CN); Chuen Pei Ng, Los Angeles, CA (US); Yiu Wa Chung, Sunshine (HK)

(73) Assignee: The Chinese University of Hong Kong, Shatin, N.T. (HK)

( * ) Notice: Subject to any disclaimer, the term of this patent is extended or adjusted under 35 U.S.C. 154(b) by 238 days.

(21) Appl. No.: 11/138,069

(22) Filed: May 25, 2005

(65) Prior Publication Data

US 2005/0287571 A1    Dec. 29, 2005

Related U.S. Application Data

(60) Provisional application No. 60/575,598, filed on May 27, 2004.

(51) Int. Cl.
 *G01N 33/53* (2006.01)
(52) U.S. Cl. .................. 435/7.1; 435/7.2; 435/7.91; 435/7.92; 436/514; 436/518
(58) Field of Classification Search .............. 435/7.1, 435/7.2, 7.91, 7.92; 436/514, 518
 See application file for complete search history.

(56) References Cited

OTHER PUBLICATIONS

Score Sequence Search Results- 2 pages (See No. 35 rat Bin 1b compared to SEQ ID No. 1 EP2D).*
Com, Emmanuelle et al.; "Expression of Antimicrobial Defensins in the Male Reproductive Tract of Rats, Mice, and Humans"; 2003, *Biology of Reproduction*, vol. 68, pp. 95-104.
Coronel, Carlos E. et al.; "Purification, Structure, and Characterization of Caltrin Proteins from Seminal Vesicle of the Rat and Mouse"; 1992, *The Journal of Biological Chemistry*, vol. 267, No. 29, pp. 20909-20915.
Dacheux, Jean-Louis et al.; "Contribution of Epididymal Secretory Proteins for Spermatozoa Maturation"; 2003, *Microscopy Research and Technique*, vol. 61, pp. 7-17.
Fouchecourt, Sophie et al.; "Stallion Epididymal Fluid Proteome: Qualitative and Quantitative Characterization; Secretion and Dynamic Changes of Major Proteins"; 2000, *Biology of Reproduction*, vol. 62, pp. 1790-1803.
Frolich, Otto et al.; "Organization of the Human Gene Encoding the Epididymis-Specific EP2 Protein Variants and its Relationship to Defensin Genes"; 2001, *Biology of Reproduction*, vol. 64, pp. 1072-1079.
Henning, Hans von Horsten et al.; "Novel Antimicrobial Peptide of Human Epididymal Duct Origin"; 2002, *Biology of Reproduction*, vol. 67, pp. 804-813.
Li, Peng et al.; "An Antimicrobial Peptide Gene Found in the Male Reproductive System of Rats"; 2001, *Science*, vol. 291, pp. 1783-1785.
Yamaguchi, Yasuhiro et al.; "Identification of Multiple Novel Epididymis-Specific β-Defensin Isoforms in Humans and Mice"; 2002, *The Journal of Immunology*, pp. 2516-2523.
Zasloff, Michael; "Antimicrobial peptides of multicellular organisms"; 2002, *Nature*, vol. 415, pp. 389-395.
Zhang, Linqi et al.; "Contribution of Human α-Defensin 1, 2, and 3 to the Anti-HIV-1 Activity of CD8 Antiviral Factor"; 2002, *Science*, vol. 298, pp. 995-1000.
Zhou, Chen Xi et al.; "An epididymis-specific β-defensin is important for the initiation of sperm maturation"; 2004, *Nature Cell Biology*, vol. 6, No. 5, pp. 458-464.

* cited by examiner

*Primary Examiner*—Mark L. Shibuya
*Assistant Examiner*—Changhwa J Cheu
(74) *Attorney, Agent, or Firm*—Townsend and Townsend and Crew LLP

(57) ABSTRACT

The present invention relates to the discovery that an epididymis-specific defensin, EP2D, plays an important role in regulating sperm motility and therefore male fertility. Provided are methods for evaluating male fertility based on the level of EP2D bound to sperm, kits for evaluating male fertility, and methods for enhancing or suppressing fertility in a male by regulating the level of EP2D and the binding between sperm and EP2D.

10 Claims, 3 Drawing Sheets

EPIDIDYMIS-SPECIFIC DEFENSIN FOR EVALUATING AND REGULATING MALE FERTILITY

RELATED APPLICATION

This application claims the benefit of U.S. provisional application No. 60/575,598, filed May 27, 2004, the contents of which are incorporated herein in the entirety.

BACKGROUND OF THE INVENTION

This invention generally relates to the evaluation and regulation of male fertility.

On one hand, it is estimated that one in every five couples in the United States has fertility problems, of which approximately 40% are due to male deficiency. The male deficiency most commonly responsible for infertility is a deficiency in sperm production both in quantity and in quality. A variety of methods have been used for treating male infertility, relying on diverse mechanisms including the induction of intracellular glutathione synthesis in the male reproductive system (U.S. Pat. No. 5,389,657), administration of human growth hormone (U.S. Pat. No. 5,250,514), administration of testosterone analogs (U.S. Pat. No. 5,596,004), and use of medicinal tea (U.S. Pat. No. 5,736,144). Additional methods and compositions are described in, e.g., U.S. Pat. Nos. 6,197,940, 6,235,783, and 6,555,140, for treating male infertility. The high prevalence of male infertility demands new and effective diagnostic and therapeutic methods.

On the other hand, prevention of unwanted pregnancy in human and other mammals is an important task in both developed and developing nations. A large number of methods and products have been developed and in wide use for this purpose. For instance, well over 100 million women each year rely on oral contraceptives to prevent unintended pregnancy. With few exceptions, these methods and products focus on suppressing female fertility. Although some new methods and compositions for controlling male fertility have been described in, e.g., U.S. Pat. Nos. 4,225,590, 5,739,124, and 6,521,641, there remains a need for developing new and effective male contraceptives.

This invention addresses these and other related needs.

BRIEF SUMMARY OF THE INVENTION

Defensins are a class of peptides known for their antimicrobial activity. The present inventors, however, discovered that defensins of epdidymis origin have an important role in sperm maturation via the polypepitdes' interaction with sperm. The present inventors discovered that the binding of epididymis-specific defensin, such as rat Bin1b and its human orthologue, the EP2D peptide, to sperm can enhance the level of male fertility. This disclosure describes various applications of this surprising discovery. In one aspect, the present invention provides a method for evaluating fertility in a male. This method comprises the following steps: (a) obtaining a biological sample from a male. This sample contains sperm and at least some of the sperm are suspected of being bound by the EP2D peptide; (b) determining the amount of the EP2D peptide bound to the sperm; and (c) comparing the amount of the EP2D peptide from step (b) with a standard control. A decrease in the amount of the EP2D peptide from the standard control indicates a lower-than-normal fertility in the male.

In an exemplary embodiment, step (b) of this method is performed by combining the sample with an antibody that specifically binds EP2D under conditions permitting the binding between the antibody and EP2D. In some cases, the antibody is attached to a detectable label. In other cases, step (b) is performed by flow cytometry, by enzyme-linked immunosorbant assay (ELISA), or determining the percentage of sperm bound by EP2D. In yet other cases, the sample and the antibody are further combined with a second antibody under conditions permitting the binding between the antibody and the second antibody, and wherein the second antibody is attached to a detectable label.

In a second aspect, the present invention provides a kit for evaluating fertility in a male. This kit generally contains the following: (a) a first container containing an antibody that specifically binds EP2D; (b) a second container containing a control sample from a male of average fertility; and (c) instruction material for the use of the kit. In some embodiments, the kit may further comprise a labeled second antibody, which binds the antibody that specifically binds to the EP2D peptide.

In a third aspect, the present invention provides a method for regulating male fertility. This method comprises the step of increasing or decreasing the level of EP2D bound to sperm, and can be used in vitro (e.g., in a semen sample prior to an artificial insemination procedure), in vivo (e.g., in the epididymis of a male), or ex vivo. In the case of in vivo administration, this method may be practiced by administering to a male a composition containing an active ingredient (i.e., a substance capable of altering the binding of EP2D and sperm) either systemically (e.g., by injection) or locally (e.g., by topical application such as a skin patch).

In some applications, the method is used to increase the level of EP2D bound to sperm, which can lead to improvement in a male's fertility level. In some embodiments, such an increase is achieved by administering to the male an EP2D peptide, which may be isolated from a natural source, recombinantly produced, or chemically synthesized, the sequence of which may consist of that of a naturally occurring EP2D sequence (e.g., set forth in SEQ ID NO:1) or may include modifications such as addition of a heterologous sequence (e.g., a tag for purification or identification purpose) or substitutions (including addition and deletion) at one or more amino acid residues within SEQ ID NO:1. In other embodiments, such an increase is achieved by administering to the male a nucleic acid that comprises a polynucleotide sequence encoding the EP2D peptide, which may be a naturally occurring sequence such as SEQ ID NO:1 or may contain modifications. This nucleic acid may be an expression vector comprising a polynucleotide sequence encoding the EP2D peptide and a promoter, which may be a constitutive promoter or an epididymis-specific promoter. In one example, the nucleic acid is a viral vector.

In other applications, the method is used to decrease the level of EP2D bound to sperm, which can lead to a reduced or completely suppressed male fertility level and can thus be used as a male contraceptive. In some embodiments, the decrease of the level of EP2D bound to sperm is achieved by administering to the male an antibody that specifically binds the EP2D peptide and prevents the binding between EP2D and sperm. In other embodiments, such a decrease is achieved by administering to the male a nucleic acid, wherein the nucleic acid comprises or encodes a nucleotide sequence that is complementary to at least a portion of the EP2D gene, e.g., an antisense DNA sequence or a small inhibitory RNA (siRNA). In some examples, the nucleic acid comprises a constitutive promoter, whereas in other examples, the promoter is epididymis-specific.

In a further aspect, the present invention provides a method for regulating male fertility by increasing or decreasing the expression level of EP2D. Compounds capable of regulating endogenous expression of EP2D can be identified and administered to a male for appropriate fertility control. These compounds may also be used in vitro, for instance, for in vitro fertilization purpose. The methods for using these compounds are similar to the methods described above for the delivery of, e.g., an EP2D peptide, an antibody against the EP2D peptide, or a nucleic acid encoding the EP2D peptide or an EP2D-specific antisense sequence.

In one additional aspect, the present invention also relates to a method for regulating male fertility by regulating the secretion of the EP2D peptide. Candidate compounds are screened for their ability to promote or suppress the secretion of EP2D in epididymis. These compounds can be subsequently administered to a male and regulate his fertility level accordingly.

DEFINITIONS

Figure 1:
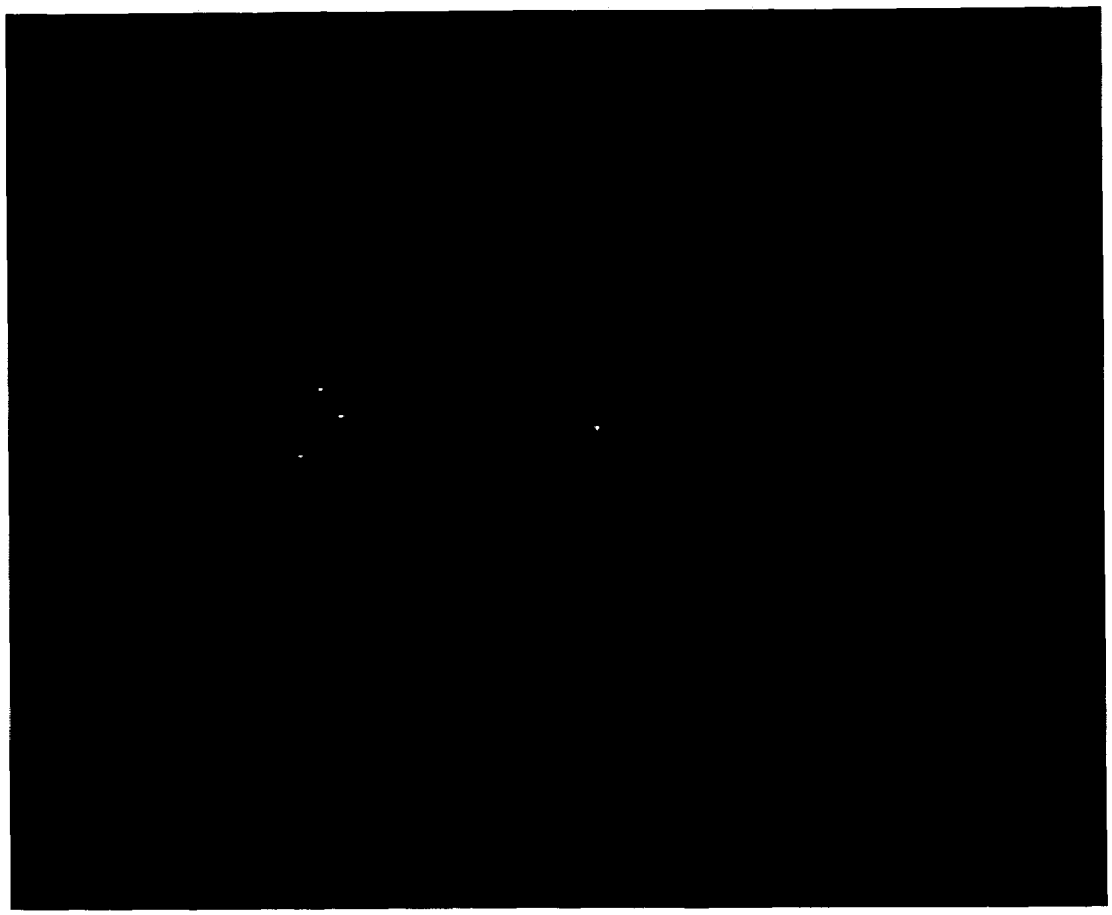
FIG. 1 Immunolocalization of human defensin EP2D in human sperm.

The term "male," as used herein, refers to a male animal, including humans and other mammals.

The term "biological sample" may include various bodily fluids, sections of tissues such as biopsy and autopsy samples, and frozen sections taken for histological purposes. Such samples may include seminal fluid, tissue, or cultured cells, e.g., primary cultures, explants, and transformed cells, from a male reproductive organ such as epididymis.

In this text, the term "EP2D" or "EP2D peptide" refers to a polypeptide comprising a core amino acid sequence that generally corresponds to the amino acid sequence of a naturally occurring defensin of epididymis origin, such as human EP2D whose sequence is set forth in SEQ ID NO:1. This core amino acid sequence may contain some variations such as amino acid deletion, addition, or substitution, but maintains a substantial level of sequence homology (e.g., at least 80%, 85%, 90%, 95%, 96%, 97%, 98%, 99%, or higher sequence homology) to SEQ ID NO:1 and is capable of promoting sperm maturation by enhancing sperm mobility. The polypeptide may further contain additional amino acid sequence, which can be heterologous in origin (e.g., an epitope tag), but retains the same functionality, i.e., capable of inducing sperm maturation. Thus, these terms encompasses the naturally occurring epididymis-specific defensin, human EP2D peptide, having the amino acid sequence of SEQ ID NO:1, as well as its homologues, orthologues, variants, and other modified versions with the same or essentially the same biological activity. The term "EP2D" may also be used to refer to a polynucleotide sequence encoding an EP2D polypeptide described above. "EP2D" polypeptide is also referred to in the art as HE2β1 or SPAG11D.

A "standard control" as used herein refers to a sample suitable for the use of a method of the present invention, in order for comparing the level of an EP2D peptide that is sperm-bound in a test sample. A sample serving as a standard control provides a profile of epididymis-specific defensin EP2D that is bound to sperm. This profile is typical for a male of a given species with average fertility at a given age. A "standard control" is established according to each individual testing method the control is to be used in.

The term "average," as used in the context of describing a male subject who provides a sample as a standard control for the claimed methods, refers to certain characteristics of fertility (e.g., sperm motility) that are representative of a randomly selected group of healthy males of the same species and similar age without any fertility-related diseases or conditions. This selected group should comprise a sufficient number of male subjects such that the average profile of epididymis-specific defensins among these males reflects, with reasonable accuracy, the corresponding profile in the general population of healthy, fertile males of the same species and similar age.

As used in this application, an "increase" or a "decrease" refers to a detectable positive or negative change in quantity from an established standard control. An increase is a positive change preferably at least 2-fold, more preferably at least 5-fold, and most preferably at least 10-fold of the control value. Similarly, a decrease is a negative change preferably at least 50%, more preferably at least 80%, and most preferably at least 90% of the control.

The term "antibody" denotes a protein of the immunoglobulin family or a polypeptide including fragments of an immunoglobulin that is capable of noncovalently, reversibly, and in a specific manner binding a corresponding antigen. An illustrative antibody structural unit includes a tetramer. Each tetramer is composed of two identical pairs of polypeptide chains, each pair having one "light" (about 25 kD) and one "heavy" chain (about 50-70 kD), connected through one or more disulfide bonds. The recognized immunoglobulin genes include the κ, λ, α, γ, δ, ε, and μ constant region genes, as well as the myriad immunoglobulin variable region genes. Light chains are classified as either ε or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively.

The term "complementarity-determining domains" or "CDRs" refers to the hypervariable regions of $V_L$ and $V_H$. The CDR is the target protein-binding site of the antibody chain that harbors specificity for that target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, *Immunology*, 4th ed., Chapter 4, W.H. Freeman & Co., New York, 2000).

The positions of the CDRs and framework regions are determined using various well known definitions in the art, e.g., Kabat, Chothia, International ImMunoGeneTics database (IMGT), and AbM (see, e.g., Johnson et al., *Nucleic Acids Res.,* 29:205-206 (2001); Chothia and Lesk, *J. Mol. Biol.,* 196:901-917 (1987); Chothia et al., *Nature,* 342:877-883 (1989); Chothia et al., *J. Mol. Biol.,* 227:799-817 (1992); Al-Lazikani et al., *J. Mol. Biol.,* 273:927-748 (1997)). Definitions of antigen combining sites are also described in the following: Ruiz et al., *Nucleic Acids Res.,* 28:219-221 (2000); and Lefranc, M. P., *Nucleic Acids Res.,* 29:207-209 (2001); MacCallum et al., *J. Mol. Biol.,* 262:732-745 (1996); and Martin et al, *Proc. Natl. Acad. Sci. USA,* 86:9268-9272 (1989); Martin et al., *Methods Enzymol.,* 203:121-153 (1991); and Rees et al., In Sternberg M. J. E. (ed.), *Protein Structure Prediction,* Oxford University Press, Oxford, 141-172 (1996).

The terms "antibody light chain" and "antibody heavy chain" denote the $V_L$ or $V_H$, respectively. The $V_L$ is encoded by the gene segments V (variable) and J (junctional), and the $V_H$ is encoded by V, D (diversity), and J. Each of $V_L$ or $V_H$ includes the CDRs as well as the framework regions.

Antibodies exist as intact immunoglobulins or as a number of well-characterized fragments produced by digestion with various peptidases. Thus, for example, pepsin digests an antibody below the disulfide linkages in the hinge region to produce $F_{(ab)}'_2$, a dimer of $F_{ab}'$ which itself is a light chain joined to $V_H$—$C_H1$ by a disulfide bond. The $F_{(ab)}'_2$ may be reduced under mild conditions to break the disulfide linkage in the hinge region, thereby converting the $F_{(ab)}'_2$ dimer into an $F_{ab}'$ monomer. The $F_{ab}'$ monomer is essentially $F_{ab}$ with part of the hinge region (Paul, *Fundamental Immunology* 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain $F_v$) or those identified using phage display libraries (see, e.g., McCafferty et al., *Nature,* 348:552-554 (1990))

For preparation of monoclonal or polyclonal antibodies, any technique known in the art can be used (see, e.g., Kohler & Milstein, *Nature,* 256:495-497 (1975); Kozbor et al., *Immunology Today,* 4:72 (1983); Cole et al., *Monoclonal Antibodies and Cancer Therapy,* pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies, and heteromeric $F_{ab}$ fragments, or scFv fragments that specifically bind to selected antigens (see, e.g., McCafferty et al., supra; Marks et al., *Biotechnology,* 10:779-783, (1992)).

The term "specifically bind," as used to describe the binding between a protein (e.g., an EP2D peptide) and an antibody produced against this protein, refers to the fact that detection of the antibody in an antigen-antibody complex under conditions permitting such binding is determinative of the presence of the protein, often in a heterogeneous population of other proteins. Under designated immunoassay conditions, a detectable signal indicating such specific binding is one that is at least twice the background signal. Thus, specific antibody-defensin binding should yield a signal at least two times, preferably more than 10 times, and more preferably more than 100 times the background.

A "detectable label" refers to a moiety capable of imparting a signal that can be registered and/or quantified by a variety of means. For instance, a detectable signal can be fluorescent and radioactive in nature; it may also be colorimetric in nature, due to an enzymatic activity the moiety comprises.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (i.e., a sequence has 80% identity, preferably 85%, 90%, 91%, 92%, 93, 94%, 95%, 96%, 97%, 98%, 99%, or 100% identity, to a reference sequence, e.g., SEQ ID NO:1), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to epididymis-specific defensin EP2D nucleic acid and protein, e.g., SEQ ID NO:1, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

An "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

A "pharmaceutically acceptable carrier" refers to an inert ingredient frequently used in a pharmaceutical preparation. A pharmaceutically acceptable carrier can be either solid, liquid, or aerosol. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material. A liquid preparation is often a solution containing pharmaceutically acceptable auxiliary substances as required to approximate physiological conditions, such as pH adjusting and buffering agents, tonicity adjusting agents, wetting agents, detergents, and the like.

DETAILED DESCRIPTION OF THE INVENTION

I. Introduction

Defensins are a class of antimicrobial peptides that play a major role in innate immunity in various multicellular organisms such as plants, insects, and mammals. Defensins are cationic peptides with a molecular weight ranging from 3 to 6 kDa and containing six cysteines paired by three disulfide bonds. They are known to participate in innate immunity against a variety of microorganisms including Gram-positive and Gram-negative bacteria, mycobacteria, many types of fungi, several enveloped viruses such as herpes simplex virus, versicular stomatitis virus, cytomegalovirus, influenza A/WSN, and human immunodeficiency virus, by rapidly killing microorganisms following permeating their membrane and impairing their ability to continue metabolic processes.

In mammals, defensins are divided into two subfamilies: α-defensins and β-defensins, which differ in the placement and connectivity of their six conserved cysteines as well as their expression patterns. α-defensins have been isolated from neutrophils and Paneth cells of the small intestine, whereas β-defensins have been found mostly in the epithelial cells in various tissue types such as the kidneys, skin, and reproductive tract of both male and female.

The present invention relates to the discovery that a defensin of epididymis origin, human EP2D and its rat counterpart Bin1b, is necessary for sperm motility and therefore necessary to ensure male fertility. New methods are therefore provided based on the EP2D-sperm interaction for evaluating the level of fertility in a male animal. New compositions and methods are also developed for enhancing male fertility by increasing the expression of an EP2D peptide and/or its binding to sperm. This discovery further allows new compositions and methods useful as male contraceptives by down-regulating the level of EP2D peptide.

Practicing this invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of an EP2D gene, a polynucleotide encoding an EP2D polypeptide, and synthetic oligonucleotides can be verified after cloning or subcloning using, e.g., the chain termination method for sequencing double-stranded templates of Wallace et al, *Gene* 16: 21-26 (1981).

II. Defensin Polynucleotide Sequence

The polynucleotide and amino acid sequence of epididymis-specific β-defensin EP2D is known and publicly available. For example, the amino acid sequence for exemplary human β-defensin EP2D is GenBank Accession No. AAG21881 or NP_478108 or AAF37187 (also referred to as SPAG11D or HE2β1). The polynucleotide sequence encoding this polypeptide is available under GenBank Accession No. AY005129 (human EP2) or NM_058201 (SPAG11D or HE2β1). The EP2D amino acid sequence is also provided in this application as SEQ ID NO:1.

A variety of methods that are well known and routinely used by those skilled in the art of biochemistry and molecular biology can be used to obtain an epididymis-specific defensin EP2D polypeptide by purification from a natural source, by chemical synthesis, or by recombinant production. Well known techniques also allow an artisan to obtain additional polynucleotide sequences encoding EP2D polypeptides of the present invention.

A. Cloning and Subcloning of a Coding Sequence for an EP2D Peptide

The rapid progress in the studies of human genome has made possible a cloning approach where a human DNA sequence database can be searched for any gene segment that has a certain percentage of sequence homology to a known nucleotide sequence, such as one encoding a previously identified human epididymis-specific defensin EP2D. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human epididymis-specific defensin, such as EP2D, can be isolated from a human cDNA or genomic DNA library using standard cloning techniques such as polymerase chain reaction (PCR), where homology-based primers can often be derived from a known nucleic acid sequence encoding an epididymis-specific defensin. Most commonly used techniques for this purpose are described in standard texts, e.g., Sambrook and Russell, supra.

cDNA libraries suitable for obtaining a coding sequence for a human epididymis-specific defensin such as EP2D may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding a defensin from the cDNA library. A general description of appropriate procedures can be found in Sambrook and Russell, supra.

A similar procedure can be followed to obtain a full-length sequence encoding a human epididymis-specific defensin such as EP2D, e.g., any one of the GenBank Accession Nos. mentioned above and possibly yet to be identified additional defeinsins closely related to EP2D, from a human genomic library. Human genomic libraries are commercially available or can be constructed according to various art-recognized methods. In general, to construct a genomic library, the DNA is first extracted from an tissue where an epididymis-specific defensin is likely found (e.g., epididymis tissue). The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology,* CRC Press Inc. 1994) to amplify a segment of nucleotide sequence from a cDNA or genomic library. Using the amplified segment as a probe, the full-length nucleic acid encoding an epididymis-specific defensin is obtained.

Relying on the same general methodology, defensin coding sequences of other species (e.g., mouse) can be obtained. Further modifications to a defensin coding sequence, e.g., nucleotide substitutions, may be subsequently made to alter the characteristics of the defensin polypeptide while retaining the desired physiological activity.

B. Modification of an Epididymis-Specific Defensin Coding Sequence

The epididymis-specific defensin EP2D polypeptide of the present invention include variants and fragments of a naturally occurring defensin, such as an EP2D peptide with the amino acid sequence of SEQ ID NO:1, that retain a similar biological activity in promoting sperm motility and sperm maturation (e.g., sperm capacitation, hyperactivation, and acrosome reaction). Such variants or fragments may exhibit at least 50%, often 80%, 90%, 100%, or greater activity relative to a reference defensin, e.g., human epididymal defensin EP2D having the sequence of SEQ ID NO:1, which are typically used in the screening methods of the invention.

In some embodiments, an EP2D variant polypeptide of the invention comprises a sequence that has at least 90% identity, typically at least 95% or at least 97% identity, preferably at least 99% identity to the region of SEQ ID NO:1 from positions 72-121 and comprises cysteine residues corresponding to the cysteine residues at positions 83, 90, 95, 105, 112, and 113 of SEQ ID NO:1. In some embodiments, the variant comprises the amino acid sequence from positions 72-133. Such variants are determined with reference to SEQ ID NO:1 using known alignment programs, e.g., the examples provided supra, or by manual alignment.

The amino acid sequence of an epididymis-specific defensin polypeptide, e.g., human EP2D as set forth in SEQ ID NO:1, may be modified while maintaining or enhancing the polypeptide's capability to promote sperm maturation, as determined by the in vitro or in vivo methods described below. Possible modifications to the amino acid sequence of a defensin polypeptide may include conservative or non-conservative substitutions; deletion or addition of one or more amino acid residues (e.g., addition at one terminal of the polypeptide of a tag sequence such as 6×His to facilitate purification or identification); truncation of a fragment ranging from approximately 2 to 10, 15, or 20 amino acids of the defensin polypeptide at either or both of the N- and C-termini; and truncation of a fragment ranging from approximately 2 to 10, 15, or 20 amino acids within the defensin polypeptide. The general strategy for making these truncation modifications is, in one series, from the N-terminus starting with the smallest truncation gradually increasing in length up to approximately 15-20 amino acids, and in another series, from the C-terminus starting with the smallest truncation gradually increasing in length up to approximately 15-20 amino acids. Upon testing the functionality of the truncated defensin polypeptides so generated in an in vitro or in vivo assay and depending on the results of such testing, one may generate additional defensin polypeptides with both N- and C-terminal truncations or with internal truncation(s) and further examine their ability to promote sperm motility and maturation.

A variety of mutation-generating protocols are established and described in the art, and can be readily used to modify a polynucleotide sequence encoding an exemplary defensin polypeptide. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

C. Modification of Nucleic Acids for Preferred Codon Usage in a Host Organism

The polynucleotide sequence encoding an epididymis-specific defensin, e.g., human EP2D, can be further altered to coincide with the preferred codon usage of a particular host. For example, the preferred codon usage of one strain of bacterial cells can be used to derive a polynucleotide that encodes a defensin polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of defensin polypeptides.

III. Production of Epididymis-Specific Defensin Polypeptides

Following verification of the coding sequence, the epididymis-specific defensin polypeptides of the present invention can be produced using routine techniques in the field of recombinant genetics, relying on the polynucleotide sequences encoding the polypeptides disclosed herein.

A. Expression Systems

To obtain high level expression of a nucleic acid encoding a defensin polypeptide of the present invention (e.g., an EP2D peptide), one typically subclones a polynucleotide encoding the defensin polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the defensin polypeptide are available in, e.g., *E. coli, Bacillus* sp., *Salmonella,* and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the defensin polypeptide in host cells. A typical expression cassette thus contains a promoter operably linked to the nucleic acid sequence encoding the defensin polypeptide and signals required for efficient polyadenylation of the transcript, ribosome binding sites, and translation termination. The nucleic acid sequence encoding the defensin polypeptide is typically linked to a cleavable signal peptide sequence to promote secretion of the defensin polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical.

Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the defensin polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an epididymis-specific defensin EP2D polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or modified defensin polypeptide or its coding sequence while still retaining the biological activity of the defensin polypeptide, e.g., the inhibitory effect toward endothelial cell proliferation. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of an epididymis-specific defensin polypeptide (e.g., an EP2D peptide), which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the epididymis-specific defensin polypeptide.

C. Detection of Recombinant Expression of a Defensin Polypeptide in Host Cells

After the expression vector is introduced into appropriate host cells, the transfected cells are cultured under conditions favoring expression of the epididymis-specific defensin polypeptide (e.g., an EP2D peptide). The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a defensin of epididymis origin (e.g., an EP2D peptide) in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a defensin polypeptide of the present invention, such as a polypeptide having the amino acid sequence of SEQ ID NO:1, (e.g., Harlow and Lane, *Antibodies, A Laboratory Manual*, Chapter 14, Cold Spring Harbor, 1988; Kohler and Milstein, *Nature*, 256: 495-497 (1975)). Such techniques require antibody preparation by selecting antibodies with high specificity against an epididymis-specific defensin polypeptide (e.g., an EP2D peptide) or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.*, 6: 511-519 (1976). More detailed descriptions of preparing antibodies against the defensin polypeptide of the present invention and conducting immunological assays detecting the defensin polypeptide are provided in a later section.

D. Chemical Synthesis of Epididymis-Specific Defensin Polypeptides

As discussed above, the amino acid sequence of a defensin polypeptide (e.g., SEQ ID NO:1) may also be modified without compromising its ability to promote sperm maturation. The epididymis-specific defensin EP2D polypeptides of the present invention, particular those that are shorter than 100-amino acid in length, thus can also be synthesized chemically using conventional peptide synthesis or other protocols well known in the art. A synthesized defensin polypeptide may have a naturally occurring defensin amino acid sequence or a modified sequence.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-(2,4-dimethoxyphenyl)-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook,* 2nd Ed., Springer-Verlag (1993)).

E. Purification of Epididymis-Specific Defensin Polypeptides

Once the expression of a recombinant defensin polypeptide in transfected host cells is confirmed, the host cells are then cultured in an appropriate scale for the purpose of purifying the recombinant polypeptide.

1. Purification of Recombinantly Produced Defensin from Bacteria

When the defensin polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., an epididymis-specific defensin polypeptide having the amino acid sequence of SEQ ID NO:1, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., an EP2D defensin polypeptide of the present invention, is expressed in host cells in a soluble form, its purification can follow the standard protein purification procedure described below. These standard purification methods are also generally applicable for purifying naturally occurring or chemically synthesized defensin polypeptides.

i. Solubility Fractionation

Often as an initial step, and if the protein mixture is complex, an initial salt fractionation can separate many of the unwanted host cell proteins (or proteins derived from the cell culture media) from the recombinant protein of interest, e.g., a defensin polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an epididymis-specific defensin EP2D polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as an epididymis-specific EP2D defensin polypeptide of the present invention) can also be separated from other proteins on the basis of their size, net surface charge, hydrophobicity, or affinity for ligands. In addition, antibodies raised against a defensin polypeptide can be conjugated to column matrices and the defensin polypeptide immunopurified. All of these methods are well known in the art.

It will be apparent to one of skill that chromatographic techniques can be performed at any scale and using equipment from many different manufacturers (e.g., Pharmacia Biotech).

IV. Immunoassays for Detection of Epididymis-Specific Defensins

To confirm the production of a recombinant epididymis-specific defensin polypeptide or to detect the presence of sperm-bound defensin, immunological assays may be a useful tool. Immunological assays are also useful for quantitatively determining the expression level of the recombinant defensin polypeptide or the level of sperm-bound defensin. Antibodies against an epididymis-specific defensin polypeptide are necessary for carrying out these immunological assays.

A. Production of Antibodies Against an Epididymis-Specific Defensin Polypeptide

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., an epididymis-specific defensin EP2D polypeptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

B. Immunoassays for Detecting Epididymis-Specific Defensins

Once antibodies specific for an epididymis-specific defensin polypeptide of the present invention are available, the amount of the polypeptide in a sample, e.g., a cell lysate or a biological sample, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

1. Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

2. Immunoassay Formats

Immunoassays for detecting a target protein of interest (e.g., an epididymis-specific defensin EP2D polypeptide) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of an epididymis-specific defensin polypeptide in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a defensin polypeptide.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

C. Flow Cytometry

Flow cytometry is one of the preferred methods for detecting defensin-bound sperm, where sperm are conjugated to suitable particles, e.g., by adsorbtion, and those with surface-bound defensin are detected through the binding of a third molecule, e.g., an antibody against the epididymis-specific defensin EP2D, which is labeled with, e.g., fluorescence. Methods of and instrumentation for flow cytometry are known in the art, and can be used in the practice of the present invention. Flow cytometry in general resides in the passage of a suspension of the microparticles as a stream past a laser beam and the detection of fluorescent emission from each particle by a photo multiplier tube. Detailed descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973).

The particles used in the practice of this invention are preferably microscopic in size and formed of a polymeric material. Polymers that will be useful as microparticles are those that are chemically inert relative to the components of the biological sample and to the assay reagents other than the binding member coatings that are affixed to the microparticle surface. Suitable microparticle materials will also have minimal autofluorescence, will be solid and insoluble in the sample and in any buffers, solvents, carriers, diluents, or suspending agents used in the assay, and will be capable of affixing to the appropriate coating material, preferably through covalent bonding. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary and particular size ranges are not critical to the invention. In most cases, the microparticles will range in diameter from about 0.5 micrometers to about 100 micrometers, and preferably from about 0.3 micrometers to about 40 micrometers.

To facilitate the particle recovery and washing steps of the assay, the particles preferably contain a magnetically responsive material, i.e., any material that responds to a magnetic field. Separation of the solid and liquid phases, either after incubation or after a washing step, is then achieved by imposing a magnetic field on the reaction vessel in which the suspension is incubated, causing the particles to adhere to the wall of the vessel and thereby permitting the liquid to be removed by decantation or aspiration. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP.

The magnetically responsive material can be dispersed throughout the polymer, applied as a coating on the polymer surface or as one of two or more coatings on the surface, or incorporated or affixed in any other manner that secures the material in to the particle. The quantity of magnetically responsive material in the particle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. An excessive quantity of magnetically responsive material in the microparticles may produce autofluorescence at a level high enough to interfere with the assay results. It is therefore preferred that the concentration of magnetically responsive material be low enough to minimize any autofluorescence emanating from the material. With these considerations in mind, the magnetically responsive material in a particle in accordance with this invention preferably ranges from about 0.05% to about 75% by weight of the particle as a whole. A more preferred weight percent range is from about 1% to about 50%, a still more preferred weight percent range is from about 2% to about 25%, and an even more preferred weight percent range is from about 2% to about 8%.

Coating of the particle surface with the appropriate assay reagent can be achieved by electrostatic attraction, specific affinity interaction, hydrophobic interaction, or covalent bonding. Covalent bonding is preferred. The polymer can be derivatized with functional groups for covalent attachment of the assay reagent by conventional means, notably by the use of monomers that contain the functional groups, such monomers serving either as the sole monomer or as a co-monomer. Examples of suitable functional groups are amine groups (—$NH_2$), ammonium groups (—$NH_3^+$ or —$NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Linkers can be used as a means of increasing the density of antibody-recognizable epitopes on the particle surface and decreasing steric hindrance. This will increase the range and sensitivity of the assay. Linkers can also be used as a means of adding specific types of reactive groups to the solid phase surface if needed to secure the particular coating materials of this invention. Examples of suitable useful functional groups are polylysine, polyaspartic acid, polyglutamic acid, and polyarginine.

In general, care should be taken to avoid the use of particles that exhibit high autofluorescence. Particles formed by conventional emulsion polymerization techniques from a wide variety of starting monomers are generally suitable since they exhibit at most a low level of autofluorescence. Conversely, particles that have been modified to increase their porosity and hence their surface area, i.e., those particles that are referred to in the literature as "macroporous" particles, are less desirable since they tend to exhibit high autofluorescence. A further consideration is that autofluorescence increases with increasing size and increasing percentage of divinylbenzene monomer.

The labels used in the labeled binding members may be any label that is capable of emitting detectable signal. Preferred such labels are fluorophores. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

The following is a list of examples of fluorophores:
4-acetamido-4'-isothiocyanatostilbene-2,2'disulfonic acid
acridine
acridine isothiocyanate
5-(2'-aminoethyl)aminonaphthalene-1-sulfonic acid (EDANS)
4-amino-N-(3-vinylsulfonyl)phenyl)naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumarin 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin diethylenetriamine pentaacetate
4,4'-diisothiocyanatodihydro-stilbene-2,2'-disulfonic acid
4,4'-diisothiocyanatostilbene-2,2'-disulfonic acid
5-(dimethylamino)naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)

fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
Phycobiliproteins (B-phycoerythrin, R-phycoerythrin, etc)
o-phthaldialdehyde
pyrene
pyrene butyrate
succinimidyl 1-pyrene butyrate
quantum dots
Reactive Red 4 (Cibacron™ Brilliant Red 3B-A)
6-carboxy-X-rhodamine (ROX)
6-carboxyrhodamine (R6G)
lissamine rhodamine B sulfonyl chloride rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives The attachment of any of these fluorophores to the binding molecules described above to form assay reagents for use in the practice of this invention is achieved by conventional covalent bonding, using appropriate functional groups on the fluorophores and on the binding members. The recognition of such groups and the reactions to form the linkages will be readily apparent to those skilled in the art.

Similarly, methods of and instrumentation for applying and removing a magnetic field as part of an automated assay are known to those skilled in the art and reported in the literature. Examples of literature reports are Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A. M., et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

V. Functional Assays

An epididymis-specific defensin polypeptide of the present invention (e.g., an EP2D peptide) has the biological activity of promoting sperm maturation, as indicated by, e.g., enhancing sperm motility, percentage of progressive movement, sperm capacitation, acrosome reaction, sperm-egg binding, and fertilizing capacity, upon its binding to sperm. In vitro assays have been described for testing a candidate polypeptide, e.g., a variant or modified version of a naturally occurring epididymis-specific defensin. See, e.g., Zhou et al., *Nature Cell Biology* 6:458-464, 2004. Briefly, sperm are first placed into sperm medium. A candidate polypeptide is subsequently added into the medium. The sperm movement is recorded and analyzed for their average-path velocity (VAP) and straight-line velocity (VSL). The presence of a defensin polypeptide that has the activity of enhancing sperm mobility and thus male fertility leads to increased VAP as well VSL.

A similar in vitro assay system measuring sperm movement may be used to test a candidate compound for its ability to enhance male fertility by promoting the binding between an epididymis-specific defensin (e.g., human EP2D) and sperm, and therefore indirectly promoting sperm maturation; on the other hand, this assay system may be used to screen for compounds that are capable of suppressing male fertility by interrupting the binding between an epididymis-specific defensin (e.g., human EP2D) and sperm, and therefore indirectly preventing sperm maturation, which leads to suppression or loss of fertility.

Another similar in vitro assay system measuring sperm movement may be used to test a candidate compound for its ability to enhance male fertility by promoting the secretion of an epididymis-specific defensin (e.g., human EP2D) thereby enhancing the binding between sperm and the defensin, and therefore indirectly promoting sperm maturation; on the other hand, this assay system may be used to screen for compounds that are capable of suppressing male fertility by interrupting the secretion of an epididymis-specific defensin (e.g., human EP2D) thereby reducing the binding between sperm and the defensin, and therefore indirectly preventing sperm maturation, which leads to suppression or loss of fertility.

Alternatively, a candidate compound may be tested in an immunological assay format for its possible role in augmenting or interrupting the binding between sperm and an epididymis-specific defensin such as human EP2D. Various immunological assays suitable for this purpose are described in an earlier section. A compound that allows increased binding is regarded as a possible enhancer of male fertility, whereas a compound causing decreased binding is regarded as a possible suppressor of male fertility. The function of such a compound is generally confirmed by the in vitro sperm mobility assay described above.

VI. Test Compounds and Screening

The present inventors revealed that binding to sperm by epididymis-specific defensin such as human EP2D or its rat orthologue Bin1b is crucial for sperm maturation and therefore for male fertility. This invention thus also provides a novel approach in identifying compounds that can improve male fertility or render male infertility by enhancing or interfering the binding between sperm and an epididymis-specific defensin. For example, antibodies against epididymis-specific defensin EP2D may prevent the sperm-defensin binding.

Another approach is to screen for compounds that cause increased or decreased epididymis-specific defensin expression. A variety of methods are known to increase the expression of a gene. Besides directly providing the gene product or a nucleic acid encoding this protein to a target tissue, compounds can identified for their ability to increase endogenous gene expression. Skilled artisans are also familiar with the means to suppress the expression of a gene. For instance, sequence-based inhibitory methods such as antisense DNA, small inhibitory RNA, and ribozyme technologies are well known and frequently practiced. A further possibility is to screen for compounds that increase or reduce the secretion of an epididymis-specific defensin such as human EP2D.

In all the above-mentioned screening methods, the candidate compounds tested can be any chemical compound (e.g., in some embodiments, small chemical compounds), or a biological entity, e.g., a macromolecule such as a protein, sugar, nucleic acid, or lipid. Thus, test compounds may be chemical molecules; combinatorial chemical libraries; nucleic acids, including oligonucleotides, etc., polypeptides, including antibodies, antibody fragments, and short peptides; extracts, e.g., from natural sources; and the like.

The assays of the invention can be designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods are employed. These methods involve providing a combinatorial library, e.g., a chemical library, containing a large number of potential therapeutic compounds. Such "combinatorial chemical libraries" are then screened in one or more assays, such as assays that measure transcript levels as described herein, to identify those library members (particular chemical species or subclasses) that display the desired characteristic activity, e.g., that increase or decrease the binding between sperm and a defensin of epididymis origin such as human EP2D. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Candidate compounds include numerous chemical classes; however, often they are small organic molecules, generally having a molecular weight of more than about 100 and less than about 2,500 daltons. Typical small molecules are less than about 2000, less than about 1500, less than about 1000, or less than about 500 daltons. The candidate compounds typically include functional groups necessary for structural interactions with proteins or nucleic acids, e.g., hydrogen bonding, and typically include at least an amine, carbonyl, hydroxyl, or carboxyl group, preferably at least two of the functional chemical groups. The candidate agents often comprise cyclical carbon or heterocyclic structures and/or aromatic or polyaromatic structures substituted with one or more of the above functional groups. Candidate compounds include peptides, saccharides, fatty acids, steroids, purines, pyrimidines, nucleic acids, and various structural analogs or combinations thereof.

In the high throughput assays of the invention, it is possible to screen thousands of different modulators in a single day. In particular, each well of a microtiter plate, e.g., a 96, 384, or 1,536-well plate, can be used to run a separate assay against a selected potential modulator, or, if concentration or incubation time effects are to be observed, every 5-10 wells can test a single modulator. Thus, a single standard microtiter plate can assay a large number of potential activators.

VII. Formulations and Administration of Pharmaceutical Compositions

The epididymis-specific defensin polypeptide (e.g., EP2D peptide) of the present invention, the polynucleotide sequences encoding such the defensin peptide, or compounds identified using the methods of the present invention as regulators of male fertility (such as a compound capable of enhancing or inhibiting sperm-defensin binding, or a compound capable of promoting or suppressing defensin expression or secretion) can be formulated to produce various pharmaceutical compositions for treating male fertility-related conditions or as male contraceptives. Possible use can be in vivo, in vitro, or ex vivo. For instance, compositions comprising an epdidymis-specific defensin EP2D polypeptide may be administered to a patient to improve his fertility; on the other hand, an EP2D polypeptide may be added into a semen sample for a proper period of incubation prior to artificial insemination, in order to improve the success rate of in vitro fertilization.

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery (e.g., by injection or skin patch) to a male reproductive organ or tissue (e.g., epididymis) at daily doses of about 0.01-5000 mg, preferably 1-500 mg, of a epididymis-specific defensin polypeptide for a 70 kg adult human per day. The appropriate dose may be administered in a single daily dose or as divided doses presented at appropriate intervals, for example as two, three, four, or more subdoses per day.

For the purpose of an in vitro fertilization procedure, a composition containing an effective amount of an epididymis-specific defensin polypeptide or a compound capable of enhancing the binding between sperm and an epididymis-specific defensin may be added to a sample containing sperm under suitable conditions for an appropriate length of time prior to contacting the sample with an egg. Typically, a defensin polypeptide ranging from about 0.01-10 µg may be added into a sperm sample before incubation.

For preparing pharmaceutical compositions containing an epididymis-specific defensin polypeptide (e.g., an EP2D peptide) or a male fertility enhancing compound, inert and pharmaceutically acceptable carriers are used. The pharmaceutical carrier can be solid, liquid, or aerosol. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an EP2D defensin polypeptide. In tablets, the active ingredient (such an EP2D defensin polypeptide or a fertility regulating compound) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active ingredient (e.g., an epididymis-specific defensin EP2D polypeptide or a male fertility regulating compound) with encapsulating material as a carrier providing a capsule in which the active ingredient (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an EP2D polypeptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing an epididymis-specific defensin polypeptide (e.g., an EP2D peptide) or a male fertility enhancer identified by a method of the present invention can be administered for prophylactic and/or therapeutic treatments. In therapeutic applications, compositions are administered to a patient already suffering from a condition related to inadequate fertility in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the defensin polypeptide or a male fertility regulating agent per day for a 70 kg patient, with dosages of from about 1 mg to about 500 mg of the polypeptide or agent per day for a 70 kg patient being more commonly used.

In prophylactic applications, pharmaceutical compositions containing an epididymis-specific defensin (e.g., human EP2D) polypeptide or a male fertility regulator are administered to a patient susceptible to or otherwise at risk of developing a disease or condition in which low fertility is a typical symptom, in an amount sufficient to delay or prevent the onset of the symptom. Such an amount is defined to be a "prophylactically effective dose." In this use, the precise amounts of the defensin polypeptide or a male fertility enhancer again depend on the patient's state of health and weight, but generally range from about 0.1 mg to about 2,000 mg of the polypeptide for a 70 kg patient per day, more commonly from about 1 mg to about 500 mg for a 70 kg patient per day.

Single or multiple administrations of the compositions of the present invention can be carried out with dose levels and pattern being selected by the treating physician. In any event, the pharmaceutical formulations should provide a quantity of an epididymis-specific defensin (e.g., human EP2D) polypeptide or a male fertility enhancer sufficient to effectively promote sperm mobility and further ensure proper sperm maturation and elevate the level of fertility in a male patient, either therapeutically or prophylatically.

Use of compositions intended as male contraceptives is similar to that described above, except that the active ingredient in these compositions tend to decrease the level of expression or secrection of an epididymis-specific defensin (e.g., human EP2D), or its interaction with sperm.

VIII. Therapeutic Applications Using Nucleic Acids

Nucleic acids encoding epididymis-specific defensins (e.g., human EP2D) can also be used in preparation of pharmaceutical compositions for treating male fertility problems or rendering male sterility. Diseases and conditions amenable to treatment by this approach may include a variety of male infertility involving, e.g., inadequate sperm mobility. For general discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding an epididymis-specific defensin (e.g., human EP2D) of the invention can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In a preferred embodiment, the polynucleotide encoding an epididymis-specific defensin polypeptide (e.g., human EP2D) can be operably linked to expression and control sequences that can direct expression of the polypeptide in the desired target host cells. Thus, one can achieve expression of the epididymis-specific defensin polypeptide under appropriate conditions in the target cell.

B. Gene Delivery Systems

Viral vector systems useful in the expression of an epididymis-specific defensin polypeptide (e.g., human EP2D or its functional variants) include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest (e.g., one encoding for an epididymis-specific defensin polypeptide of the present invention) are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as aDNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of an epididymis-specific defensin polypeptide of the invention (e.g., human EP2D or its functional variants) into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.,* 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,*

81:6349-6353 (1984); Danos and Mulligan *Proceedings of the National Academy of Sciences, USA*, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding an epididymis-specific defensin polypeptide (e.g., an EP2D polypeptide) is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations containing a nucleic acid encoding an epididymis-specific defensin polypeptide of the invention (e.g., an EP2D peptide) can be delivered to any tissue or organ using any delivery method known to the ordinarily skilled artisan. In some embodiments of the invention, the nucleic acid encoding an epididymis-specific defensin polypeptide (e.g., human EP2D or its functional variants) are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6): 2414-9 (1996); Koc et al., *Seminars in Oncology* 23(1):46-65 (1996); Raper et al., *Annals of Surgery* 223(2):116-26 (1996); Dalesandro et al., *J. Thorac. Cardi. Surg.*, 11(2):416-22 (1996); and Makarov et al., *Proc. Natl. Acad. Sci. USA* 93(1): 402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 µg-10 mg, or 30-300 µg DNA per patient are typical. Doses generally range between about 0.01 and about 50 mg per kilogram of body weight, preferably between about 0.1 and about 5 mg/kg of body weight or about $10^8$-$10^{10}$ or $10^{12}$ particles per injection. In general, the dose equivalent of a naked nucleic acid from a vector is from about 1 µg-5000 µg for a typical 70 kg patient, and doses of vectors which include a retroviral particle are calculated to yield an equivalent amount of nucleic acid encoding an epididymis-specific defensin polypeptide (e.g., a human EP2D peptide or its functional variants).

IX. Kits

The present invention can be practiced conveniently by using kits. The kits may contain, at the option of the provider, the components for practicing the invention. The kits may contain, for example, one or more containers, such as microcentrifuge tubes, containing an antibody suitable for detecting a defensin of epididymis origin described in the present disclosure (e.g., human EP2D), as well as a standard control. A standard control can include, e.g., a positive control such as a recombinant or synthesized EPD2 peptide. Additional components, such as solutions or enzyme(s), necessary for the detection of sperm-bound defensin, may also be included. Furthermore, the kits contain written instructions for practicing the invention either as an insert or on a label on the package or on items within the packaging.

Kits comprising pharmaceutical compositions of the present invention are also provided. The kits may contain, for example, one or more containers containing a composition comprising a pharmaceutically acceptable carrier and an effective amount of an epididymis-specific defensin polypeptide (e.g., an EP2D peptide), a nucleic acid encoding such a polypeptide, or a compound identified by using a method of the present invention as a male fertility regulator. The kit may also contain written instructions on how to dispense the pharmaceutical composition, including description of the type of patients who may be suitable for the treatment (e.g., a person having fertility related conditions or a person seeking a male contraception), the schedule (e.g., dose and frequency) and route of administration, and the like.

X. Non-Human Transgenic Animals

The present invention also relates to non-human transgenic animals, which have additional copies of an epididymis-specific defensin gene (such as human EP2D) that lead to increased gene expression of the defensin or, in the alternative, have the epididymis-specific defensin gene deleted (i.e., knocked out) such that the expression of such defensin is eliminated. Accordingly, these transgenic animals may be either highly fertile or essentially sterile.

The general methods of generating transgenic animals have been well established and frequently practiced. The following sections provide a brief description of some of the well known techniques to generate transgenic non-human mammals for the purpose of illustration, not limitation.

A. Targeting of the Disruption: Homologous Recombination

The process of homologous recombination can be used to control the site of integration of a transgene, i.e., a nucleic acid comprising the coding sequence of a selection marker, into the location of the endogenous defensin coding sequence of an animal cell and thereby disrupt that gene and prevent its normal expression. Homologous recombination is described in detail by Watson in *Molecular Biology of the Gene*, 3rd Ed., W.A. Benjamin, Inc., Menlo Park, Calif. (1977).

Homologous recombination is exploited by a number of various methods of "gene targeting" well known to those of skill in the art (see, e.g., Mansour et al., *Nature* 336:348-352 (1988); Capecchi et al., *Trends Genet.* 5:70-76 (1989); Capecchi, *Science* 244:1288-1292 (1989); Capecchi et al., *Current Communications in Molecular Biology*, pp 45-52, Capecchi, M. R. (ed.), Cold Spring Harbor Press, Cold Spring Harbor, N.Y. (1989); Frohman et al., *Cell* 56: 145-147 (1989)). Some approaches further involve increasing the frequency of recombination between two DNA molecules by treating the introduced DNA with agents that stimulate recombination (e.g., trimethylpsoralen, IJY light, etc.), most approaches, however, utilize various combinations of selectable markers to facilitate isolation of the transformed cells.

The same general methods can be used to replace both alleles of the encoding sequence for an epididymis-specific defensin such as an orthologue of human EP2D. The frequency of such dual recombination events is, however, significantly lower. Animals with a single allele substitution can be cross-bred to produce homozygotes with both alleles disrupted.

B. Transformation of Cells

To produce the transgenic animals of the present invention, cells are transformed with a construct containing the transgene comprising an epididymis-specific defensin coding sequence, or a construct containing a selection marker that aims to disrupt an endogenous defensin gene. In this context, the term "transformed" is defined as introduction of exogenous DNA into a target cell by any means known to the skilled artisan. These methods of introduction include, but are not limited to, transfection, microinjection, infection (with, for example, retroviral-based vectors), electroporation, and microballistics. The term "transformed," unless otherwise indicated, is not intended herein to indicate alterations in cell behavior and growth patterns accompanying immortalization, density-independent growth, malignant transformation or similar acquired states in culture.

To create animals having a particular gene substituted in all cells, it is preferable to introduce a transgene construct into the germ cells (sperm or eggs, i.e., the "germ line") of the desired species. Genes or other DNA sequences can be introduced into the pronuclei of fertilized eggs by microinjection or other methods as described below. Following pronuclear fusion, the developing embryo may carry the introduced gene in all its somatic and germ cells since the zygote is the mitotic progenitor of all cells in the embryo.

Several general methods of cell transformation are described as follows. These methods can be used for introduction of an additional defensin gene or for knocking out an defensin gene, even though in individual sentences only introduction or knockout is mentioned as the purpose.

1. Microinjection Methods

Microinjection is one preferred method for transformation of a zygote. The epididymis-specific defensin gene, e.g., one encoding human EP2D, being introduced by this method need not be incorporated into any kind of self-replicating plasmid or virus (Jaenisch, *Science* 240:1468-1474 (1988)). Once the DNA molecule has been injected into the fertilized egg, the egg is implanted into the uterus of a recipient female and allowed to develop into an animal. Since all of the animal's cells are derived from the implanted fertilized egg, all of the cells of the resulting animal (including the germ line cells) shall contain the introduced defensin gene. If, as occurs in about 30% of events, the first cellular division occurs before the defensin gene has integrated into the cell's genome, the resulting animal will be a chimeric animal. By breeding and inbreeding such animals, it is possible to routinely produce heterozygous and homozygous transgenic animals.

2. Retroviral Methods

Retroviral infection is another means to introduce a transgene into a non-human mammal. The developing non-human embryo can be cultured in vitro to the blastocyst stage. During this time, the blastomeres can be targets for retroviral infection (Jaenich, *Proc. Natl. Acad. Sci. USA* 73:1260-1264 (1976)). The viral vector system used to introduce the transgene, e.g., an epididymis-specific defensin gene such as human EP2D, is typically a replication-defective retrovirus (Jahner et al., *Proc. Natl. Acad. Sci. USA* 82:6927-6931 (1985); Van der Putten et al., *Proc. Natl. Acad. Sci. USA*, 82:6148-6152 (1985)). Transfection is easily and efficiently obtained by culturing the blastomeres on a monolayer of virus-producing cells (Van der Putten et al., supra; Stewart et al., *EMBO J.,* 6:383-388 (1987)). Alternatively, infection can be performed at a later stage. Virus or virus-producing cells can be injected into the blastocoele (Jahner et al., *Nature* 298:623-628 (1982)). In addition, it is also possible to introduce transgenes into the germ line, albeit with low efficiency, by intrauterine retroviral infection of the midgestation embryo (Jahner et al., supra).

3. ES Cell Implantation

A third and preferred target cell for transgene introduction is the embryonic stem cell (ES). ES cells are obtained from pre-implantation embryos cultured in vitro and fused with embryos (Evans et. al., *Nature* 292:154-156 (1981); Bradley et al., *Nature* 309:255-258 (1984); Gossler et al., *Proc. Natl. Acad. Sci. USA* 83:9065-9069 (1986); and Robertson et al., *Nature* 322:445-448 (1986)). Transgenes can be efficiently introduced into the ES cells by a number of means well known to those of skill in the art. In order to facilitate the recovery of those cells that have received the nucleic acid containing the transgene, it is preferable to introduce the nucleic acid containing the transgene, e.g., an epididymis-specific defensin gene such as human EP2D, in combination with a second gene encoding a detectable marker. Preferably, the detectable marker gene will be expressed in the recipient cell and result in a selectable phenotype. Numerous selectable markers are well known to those of skill in the art. The detectable marker gene may also be any gene that can compensate for a recognizable cellular deficiency.

Any ES cell may be used in accordance with the present invention. It is, however, preferred to use primary isolates of ES cells. ES cell lines may be derived or isolated from any mammals such as rodents, rabbits, sheep, goats, fish, pigs, cattle, and primates. Cells derived from rodents (i.e. mouse, rat, hamster, etc.) are preferred.

C. Production of Transgenic Animals via Somatic Cell Nuclear Transfer

Production of the transgenic animals of this invention is not dependent on the availability of ES cells, as these animals can be produced using methods of somatic cell nuclear transfer. For example, a somatic cell can be obtained from the species in which the native epididymis-specific defensin gene (such as an orthologue of the human EP2D gene) is to be disrupted. The cell is first transfected with a construct that introduces a detectable marker into the location of the endogenous defensin gene, e.g., via heterologous recombination. Cells harboring the newly introduced exogenous gene are selected as described above. The nucleus of such a transformed cell is then placed in an unfertilized enucleated egg (e.g., an egg from which the natural nuclei have been removed by microsurgery). Once the transfer is complete, the recipient egg contains a complete set of genes, just as they would if they had been fertilized by sperm. The eggs are then cultured for a period before being implanted into a host mammal (of the same species that provided the egg) where they are carried to term, culminating in the berth of a transgenic animal comprising a nucleic acid construct containing the disrupted epididymis-specific defensin gene.

The production of viable cloned mammals following nuclear transfer of cultured somatic cells has been reported for a wide variety of species including, but not limited to calves (Kato et al., *Science* 262:2095-2098 (1998)), sheep (Campbell et al., *Nature* 380:64-66 (1996)), mice (Wakayama and Yanagimachi, *Nat. Genet.* 22:127-128 (1999)), goats (Baguisi et al., *Nat. Biotechnol.* 17:456-461 (1999)), monkeys (Meng et al., *Biol. Reprod.* 57:454-459 (1997)), and pigs (Bishop et al., *Nature Biotechnol.* 18:1055-1059 (2000)). Nuclear transfer methods have also been used to produce clones of transgenic animals. Thus, for example, the production of transgenic goats carrying the human antithrobin III gene by somatic cell nuclear transfer has been reported (Baguisi et al., *Nature Bioiechnol.* 17:456-461 (1999)).

Using methods of nuclear transfer as described in these and other references, cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass (CICM) cells. The cloned embryos can also be combined with fertilized embryos to produce chimeric embryos, fetuses, and/or offspring.

Somatic cell nuclear transfer also allows simplification of transgenic procedures by working with a differentiated cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques.

Mammalian cells useful in the present invention may be obtained by well known methods. They include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the mammalian cells used for nuclear transfer may be obtained from different organs, e.g., skin, lung, pancreas, liver, stomach, intestine, heart, reproductive organs, bladder, kidney, urethra, and other urinary organs. Suitable donor cells, i.e., cells useful in the subject invention, may be obtained from any cell or organ of the body, including all somatic or germ cells.

The methods for embryo transfer and recipient animal management for somatic cell nuclear transfer are standard procedures used by those skilled in the art. For review see, Siedel, G. E., Jr., "Critical review of embryo transfer procedures with cattle" in *Fertilization and Embryonic Development in Vitro*, page 323, L. Mastroianni, Jr. and J. D. Biggers, ed., Plenum Press, New York, N.Y. (1981).

EXAMPLES

The following examples are provided by way of illustration only and not by way of limitation. Those of skill in the art will readily recognize a variety of non-critical parameters that could be changed or modified to yield essentially similar results.

Introduction

Although the role of the epididymis, a male accessory sex organ, in sperm maturation has been established for nearly four decades (Orgebin-Crist, M. C., *Nature* 216, 816-818 (1967)), the maturation process itself has not been linked to a specific molecule of epididymal origin. Here we show that Bin1b, a rat epididymis-specific β-defensin and the orthologue of human EP2D with antimicrobial activity (Li et al., *Science* 291, 1783-1785 (2001)), can bind to the sperm head in different regions of the epididymis with varied binding patterns. In addition, Bin1b-expressing cells, either of epidymal origin or from a Bin1b-transfected cell line, can induce progressive sperm motility in immotile immature sperm. This induction of motility is mediated by the Bin1b-induced uptake of $Ca^{2+}$, a mechanism that has a less prominent role in maintaining motility in mature sperm. In vivo antisense experiments show that suppressed expression of Bin1b results in reduced binding of Bin1b to caput sperm and in considerable attenuation of sperm motility and progressive movement. Thus, β-defensin is important for the acquisition of sperm motility and the initiation of sperm maturation.

Results

Mammalian sperm are produced in the testis, but they can neither swim nor fertilize an egg when they leave the testis. They become mature and acquire their forward motility and fertilizing capacity during transit through the epididymis, situated next to the testist (Orgebin-Crist, M. C., *Nature* 216, 816-818 (1967); Bedford, J. M., *Nature* 213, 1097-1099 (1967)). The epididymal fluid milieu, which is created by specialized regions of the epididymis—namely, the caput (head), corpus (body) and cauda (tail)—is thought to be essential for sperm maturation; however, the molecular basis for the maturation process remains largely unknown. Of about 200 epididymal proteins present in different species, few have been identified that seem to be directly involved in sperm maturation in the epididymis (Fouchecourt et al., *Biol. Reprod.* 62, 1790-1803 (2000); Dacheux et al., *Microsc. Res. Tech.* 61, 7-17 (2003)).

Bin1b is a rat epididymis-specific peptide (Li et al., *Science* 291, 1783-1785 (2001)) with known orthologues in human (see, e.g., von Horsten et al., *Biol. Reprod.* 67, 804-813 (2002)), among which the closest related orthologue is human EP2D (Frohlich et al., *Biol Reprod.* 64(4):1072-9 (2001)). We have previously shown that Bin1b has molecular structure and antimicrobial activity similar to those of β-defensins (Li et al., *Science* 291, 1783-1785 (2001)). The region-specific localization of Bin1b, which is expressed exclusively in the middle of the caput region and not in other regions of the epididymis, led us to the hypothesis that Bin1b might have a role in sperm maturation other than merely being a β-defensin, because the microenvironment of the caput region has been shown to be essential for sperm to acquire their forward motility (Jeulin et al., *Cell Motil. Cytoskeleton* 35, 147-161 (1996); Yeung et al., *J. Reprod. Fertil.* 96, 427-441 (1992)).

As its signal sequence suggests that it is a secretory peptide, we considered that Bin1b might affect sperm maturation by directly binding to sperm. We tested this possibility by immunohistochemical assessment with a Bin1b antibody, the specificity of which was verified by western blot. Immunostaining for human EP2D showed that the human orthologue of Bin1b indeed binds sperm (FIG. 1). Bin1b immunoreactivity was found in sperm from all epididymal regions except the initial segment, and the percentage of sperm binding to Bin1b antibody, determined by flow cytometry, varied across the different regions. The patterns of sperm binding also varied within the different regions, with immunoreactivity distributed throughout the caput sperm head and prominent signals concentrated on the post-acrosome region of cauda sperm. These distinct sperm-binding patterns of Bin1b in different regions suggest that Bin1b may modify specific sperm function during their transit through the epididymis.

We investigated possible effects of Bin1b on sperm maturation by using the epididymal epithelial cell culture previously used for elucidating the antimicrobial activity of Bin1b (Li et al., *Science* 291, 1783-1785 (2001)). Caput epididymal cells expressing Bin1b and control cauda epididymal cells were cultured and grown to confluence on a floating filter device to ensure formation of epithelial polarity and proper epididymal secretion. Immature sperm, collected from the initial segment of the epididymis, were then added to the apical compartment of the epididymal culture and incubated for various durations. Sperm motility dynamics, which is the most obvious maturational change in sperm (Yeung et al., in *Molecules to Clinical Practice* (eds Robaire, B. & Hinton, B.) 417-434 (Plenum, New York, 2002)), was examined by computer-assisted sperm analysis.

Figure 2:
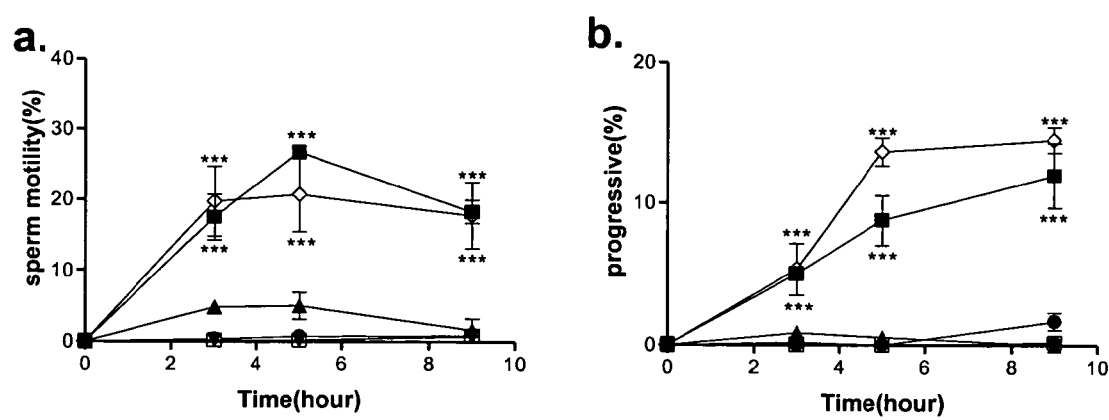
FIG. 2 Effect of Bin1b, a rat orthologue of EP2D, on sperm motility. Sperm motility (a) and percentage of progressive movement (b) induced by coculture with defensin-expressing caput epididymal epithelial cells, but not the control cauda cells, were greatly attenuated by the antibody against EP2D rat orthologue (1:800). ■: cocultured with caput cell, ▲: cocultured with cauda cell, ▼: cocultured with caput cell treated with the antibody, ○: cocultured with caput cell treated with preimmune serum.
Figure 3:
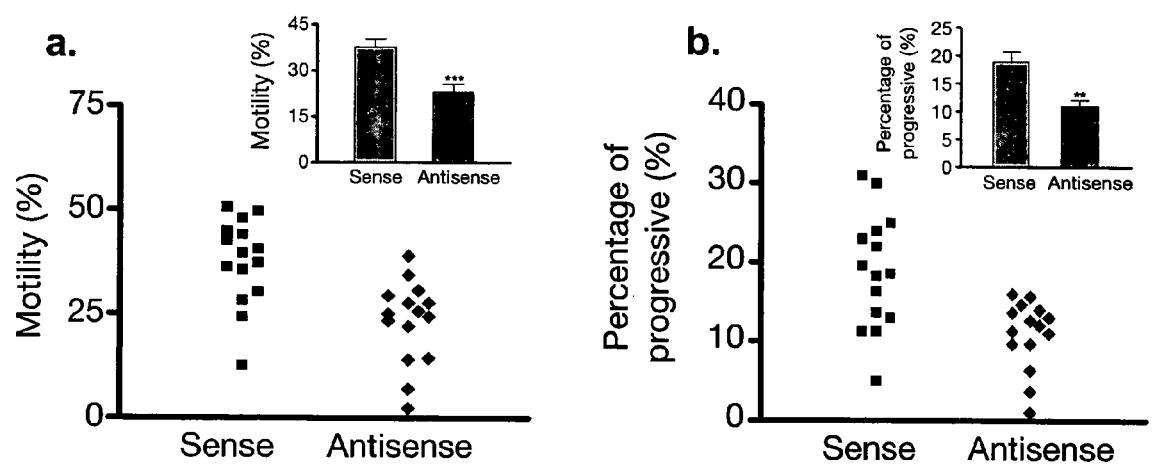
FIG. 3 Effect of In vivo suppression of EP2D rat orthogue on sperm motility. Distribution of results of sperm motility (a) and percentage of progressive movement (b) obtained from sense control and antisense samples, with corresponding summary in the insert, showing reduced sperm motility after suppression of EP2D rat orthologue in vivo by antisense. Data expressed as mean±SEM (n=5-15; Unpaired T-test). *P<0.05, P<0.01, *P<0.0001.

The immature sperm showed non-progressive movement when first released into sperm medium and stopped beating within a few minutes, consistent with previous observations (Yeung et al., *Mol. Reprod. Dev.* 38, 347-355 (1994)). The immotile sperm began to move, however, 3 h after coculture with caput (but not cauda) epididymal epithelial cells and reached a plateau at 5 h, which could be maintained for up to 9 h (FIG. 2a). Analysis of the sperm movement parameters showed that both averaged-path velocity (VAP) and straight-line velocity (VSL) were significantly greater in sperm cocultured with caput cells than in those cocultured with cauda cells (Table 1). By contrast, there was basically no sperm movement when sperm were incubated in sperm medium or fresh culture medium for epithelial cells (FIG. 2a).

Because progressive movement of sperm is a characteristic of sperm maturation (Yeung et al., in *Molecules to Clinical Practice* (eds Robaire, B. & Hinton, B.) 417-434 (Plenum, New York, 2002)), we determined the effects of caput cells on progressive movement. In the presence of caput cells, sperm acquired slow progressive motility at 3 h, which increased further and could be sustained for up to 9 h, whereas no significant change in progressive movement was observed after other cell treatments (FIG. 2b). Thus, by coculturing with caput epididymal cells in vitro, immotile immature sperm could be induced to acquire and sustain progressive motility.

To determine whether the increased sperm motility and gain of progressive movement were due to the effects of Bin1b, we incubated the cocultures with an antibody against Bin1b. Treatment with Bin1b antibody reversed the increase in sperm motility and the gain of progressive movement induced by caput cells, whereas no significant changes in these parameters were observed when the cocultures were treated with control preimmune serum (FIG. 2a, b). These results indicate that Bin1b has a role in inducing sperm motility in immature sperm.

To confirm this role of Bin1b and to exclude the involvement of other factors secreted by caput epididymal cells, we transfected the Bin1b complementary DNA into a colonic epithelial cell line, T84, that does not express Bin1b endogenously. A cell line stably expressing Bin1b (Bin-T84) and a control cell line transfected with empty expression vector (Vet-T84) were generated, and expression of Bin1b was confirmed by polymerase chain reaction with reverse transcription (RT-PCR). Sperm coculture experiments were then conducted with immotile immature sperm, as described above.

The increases in sperm motility and percentage of progressive movement, as well as the time course of these increases, were similar in sperm cocultured with Bin-T84 cells and sperm cocultured with caput epididymal cells (FIG. 2a, b); by contrast, no significant increase was observed in cocultures with Vet-T84 cells or when Bin1b antibody was present. Positive Bin1b immunoreactivity was observed in more than 80% of immature sperm (which initially stained negative for Bin1b) after 1 h of incubation with Bin-T84 conditioned medium containing secreted Bin1b. By contrast, no significant increase in Bin1b immunoreactivity was found in mature sperm from the cauda region that initially stained positive for Bin1b. Taken together, the coculture experiments with caput epididymal cells and with Bin-T84 cells confirm our hypothesis that Bin1b is involved in the sperm maturation process at the point where immature sperm start to gain progressive motility; a characteristic change in sperm movement that is known to be associated with sperm from the distal caput epididymis (Yeung et al., in *Molecules to Clinical Practice* (eds Robaire, B. & Hinton, B.) 417-434 (Plenum, New York, 2002)). The involvement of Bin1b in the initiation of sperm maturation may explain why this β-defensin is expressed exclusively in the middle caput region.

We considered how Bin1b might mediate this change in sperm motility. Defensins are well-characterized cationic (polar) molecules with spatially separated hydrophobic and charged regions that allow them to insert into phospholipid membranes and to form holes or channels in biological membranes. This mechanism of action underlies the antimicrobial capability of defensins (Zasloff, M., *Nature* 415, 389-395 (2002)), which have also been shown to modulate membrane ion channels, including the activation of L-type $Ca^{2+}$ channels (MacLeod et al., *Proc. Natl. Acad. Sci. USA* 88, 552-556 (1991); Bateman et al., *J. Biol. Chem.* 271, 10654-10659 (1996)). Thus, Bin1b might either form $Ca^{2+}$-permeable channels or activate $Ca^{2+}$ channels in sperm, thereby enabling sperm to accumulate $Ca^{2+}$, which is well known to have a central role in sperm function, including sperm motility, sperm capacitation and the acrosome reaction (Guraya, S. S., *Int. Rev. Cytol.* 199, 1-64 (2000); Breitbart, H., *Mol. Cell. Endocrinol.* 187, 139-144 (2002)).

It has been reported that a marked change in the $Ca^{2+}$-accumulating capacity of sperm occurs during their transit through the epididymis (Hoskins et al., *J. Submicrosc. Cytol.* 15, 21-27 (1983)) and that the $Ca^{2+}$ concentration of Caput sperm is about twofold higher than that of cauda sperm (Vijayaraghavan et al., *Reprod. Nutr. Dev.* 24, 81-94 (1984)). Caput sperm also accumulate $Ca^{2+}$ from exogenous sources at a rate that is 2-4 times faster than that of cauda sperm". In addition, a $Ca^{2+}$-dependent mechanism has been implicated in the transformation of an irregular movement of caput sperm into a progressive movement during epididymal sperm maturation (Serres, C. et al. *Reprod. Nutr. Dev.* 24, 81-94 (1984); Peterson et al., *Fertil. Steril.* 27, 1301-1307 (1976)); however, the mechanism underlying $Ca^{2+}$ transport through the sperm membrane during maturation is not clear.

We therefore considered that Bin1b-formed ion channels or Bin1b-activated $Ca^{2+}$ channels might provide a pathway for a $Ca^{2+}$ influx required for inducing sperm motility. To test this hypothesis, we first examined the $Ca^{2+}$ dependence of the Bin1b effect on sperm motility. When $Ca^{2+}$-free medium was used in the coculture experiments with caput epididymal cells or Bin-T84 cells, no increase in sperm motility or progressive movement (data not shown) was observed for up to 9 h. When $Ca^{2+}$ was added back to the medium at 3 h, however, an increase in both sperm motility and progressive movement (data not shown) was observed 2 h after the addition, indicating that the Bin 1 b effect on sperm motility depends on extracellular $Ca^{2+}$. These results indicate that Bin1b may be able to regulate $Ca^{2+}$ uptake in sperm.

Incubating the immature sperm with Bin-T84-conditioned medium, but not control Vet-T84-conditioned medium, resulted in a concentration-dependent increase in $Ca^{2+}$ uptake that could be substantially blocked by Bin1b antibody or the L-type $Ca^{2+}$ channel blockers nifedipine (0.5 µM) and verapamil (1 µM), but not by the T-type $Ca^{2+}$ channel blocker pimozide (1 µM). Similarly, nifedipine and verapamil significantly reduced Bin1b-induced sperm motility, whereas pimozide was less effective. The dependence of Bin1b-induced sperm motility on extracellular $Ca^{2+}$ the ability of Bin-T84 conditioned medium to induce sperm $Ca^{2+}$ uptake, and the inhibition of the Bin1b effect by $Ca^{2+}$ channel blockers indicate that Bin1b may activate sperm $Ca^{2+}$ channels, leading to the $Ca^{2+}$ influx necessary for immature sperm to acquire motility.

The distinct binding patterns of Bin1b to sperm in different epididymal regions—for example, its concentration on the post-acrosome region of cauda sperm versus its uniform distribution throughout the head of caput sperm-prompted us to examine whether Bin1b contributes to the maintenance of motility in mature cauda sperm. We examined the effect of Bin-T84 conditioned medium on the $Ca^{2+}$ uptake of mature sperm from the cauda region, but observed no significant increase in $Ca^{2+}$ uptake during the incubation period. Sperm collected from the cauda epididymal region showed well-documented vigorous sperm motility, of which only about 20% could be inhibited by Bin1b antibody, in contrast to the inhibition of more than 90% observed in stimulated immature sperm (FIG. 2a). Notably, 0.5 µM nifedipine, which greatly suppressed Bin1b-induced motility in immature sperm, did not have a pronounced effect on cauda sperm motility, at least, not to the same extent as Bin1b antibody. These results have two implications: first, unlike its essential role in inducing sperm motility in immature sperm, Bin1b is relatively less important in maintaining sperm motility in mature sperm; second, the action of Bin1b on cauda sperm may be different from its action on caput sperm in that it may involve other $Ca^{2+}$ channels. In short, it seems that mechanisms other than Bin1b may develop during sperm maturation and become important for the maintenance of motility in mature sperm.

To confirm the role of Bin1b in the acquisition of sperm motility in a physiological context, we used an antisense oligonucleotide directed against Bin1b to reduce Bin1b expression in vivo and examined its effect on sperm motility and progressive movement. As compared with a sense control, the antisense Bin1b oligonucleotide (20 µg ml$^{-1}$) significantly suppressed the expression of Bin1b messenger RNA in the caput epididymis, as assessed by semiquantitative RT-PCR; this decrease in expression resulted in a considerable reduction in Bin1b binding to sperm collected in the distal caput region, as shown by immunofluorescence staining in conjunction with flow cytometry. Consistent with the reduction in Bin1b expression and sperm binding, the motility and progressive movement of sperm taken from the distal caput epididymis in rats treated with Bin1b antisense oligonucleotide were also found to be significantly lower than those of the sperm from the control treated with sense oligonucleotide (FIG. 4a, b). Taken together, our in vitro and in vivo studies confirm that Bin1b is essential for the acquisition of sperm motility and thus the initiation of sperm maturation.

Our findings are consistent with the long-recognized central role of $Ca^{2+}$ in sperm motility and provide insight into the possible mechanism that regulates sperm $Ca^{2+}$ uptake, pertinent to the acquisition of sperm motility. Bin1b binding to sperm seems to activate $Ca^{2+}$ channels and to allow $Ca^{2+}$ uptake, leading to the initiation of sperm motility in immature sperm. Sperm $Ca^{2+}$ uptake is considered to be one of the changes that accompanies sperm maturation in the epididymis, and our findings are consistent with the previously observed higher rate of $Ca^{2+}$ accumulation (Vijayaraghavan et al., *Biol. Reprod.* 40, 744-751 (1989)) and higher $Ca^{2+}$ concentration (Vijayaraghavan et al., *Reprod. Nutr. Dev.* 24, 81-94 (1984)) in caput sperm as compared with cauda sperm. Our results also suggest that Bin1b does not contribute either to $Ca^{2+}$ uptake or to maintaining motility in mature cauda sperm. The differential effect of Bin1b on immature and mature sperm may be due to the changes in its binding pattern to sperm, which in turn may reflect modification of the sperm membrane; a process that is known to be associated with sperm maturation (Hammerstedt et al., *Biol. Reprod.* 27, 745-754 (1982)). Overall, Bin1b seems to be involved in the first uptake of $Ca^{2+}$ that is responsible for the acquisition of motility by immature sperm and, to a much lesser extent, the maintenance of motility in mature sperm.

Our results suggest that Bin1b, an epididymis-specific β-defensin, is not limited to killing bacteria (Li et al., *Science* 291, 1783-1785 (2001)) but is also involved in sperm maturation in the epididymis. Our results such as the immunohistochemical assay shown in FIG. 1 further lead us to believe that the human orthologue of Bin1b, EP2D, is also involved in the sperm maturation process. By regulating the level of EP2D, the level of male fertility can therefore be regulated. Although exactly how epididymis-specific defensins maintain their dual capacity: anti-bacterial activity and promoting sperm maturation, is yet to be fully illustrated, we speculate that different modes of action may be exploited by the defensins, such as Bin1b or EP2D, under different conditions; in other words, the ever-changing fluid in different regions of the epididymis and the altered environment upon bacterial infection may lead to different modes of defensin action. This is because the electrostatic charge interaction within the cell membrane that is required for the initial action of defensins is crucially dependent on the ionic strength of the fluid milieu (Zasloff, M., *Nature* 415, 389-395 (2002)). Although the detailed mechanisms of Bin1b action remain to be elucidated, the observed dual effects of Bin 1b attest to the importance of this β-defensin in the epididymis. Other studies have also identified a few region-specific β-defensins in human and mouse epididymides, supporting the notion that they may contribute to epididymal regulation as well as innate immunity (Yamaguchi et al., *J. Immunol.* 169, 2516-2523 (2002); Com et al., *Biol. Reprod.* 68, 95-104 (2003)). Notably, the antimicrobial peptide caltrin, which originates from the seminal vesicle, has been also shown to affect sperm capacitation and fertilization (Coronel et al., *J. Biol. Chem.* 267, 20909-20915 (1992)). Further investigation of the roles of defensins may shed new light on our understanding of the sperm maturation process and its regulation. Defensins, such as Bin1b, may not only have therapeutic implications for sexually transmitted diseases (Zasloff, M., *Nature* 415, 389-395 (2002); Zhang et al., *Science* 298, 995-1000 (2002)) but also offer an interesting lead for work on male infertility and contraception.

TABLE 1

Comparison of movement parameters between immature rat caput sperm cocultured with caput and cauda epididymal epithelial cells. Data were obtained using computer-assisted sperm analysis (CASA) and expressed as mean ± SEM.

| Parameters | Time | Caput co-culture | Cauda co-culture |
|---|---|---|---|
| VAP | 5 hr | 125.4 ± 3.08* | 80.6 ± 16.5 |
| (μm/s) | 9 hr | 143.3 ± 11.0 | 80.7 ± 35.5 |
| VSL | 5 hr | 72.9 ± 1.5** | 58.8 ± 4.0 |
| (μm/s) | 9 hr | 68.18 ± 2.8* | 37.7 ± 16.1 |

*$P < 0.05$,
**$P < 0.01$, unpaired T test. Compared with corresponding cauda values.
VAP = averaged path velocity (μm/s),
VSL = straight line velocity (μm/s).

Methods

Selection of EP2D peptide for immunogen. A 16mer peptide C113-D128, CVSNTDEEGKEKPEMD (SEQ ID NO:2), was selected based on a number of parameters, including predicted antigenicity, hyrdrophilicity, flexibility, and the likelihood of beta-turns. First, the Kyle-Little hydrophobicity screen was performed to reveal the hydrophilic region of the EP2D protein, then the Chou-Fasman screen were performed to reveal the region that has high propensity for beta-turns. For further selection refinement, preferred peptides were selected based on these following further criteria:

1. Accessibility of antigen: The protein is screened for binding motifs that may block access to the antigen in vivo, including transmembrane regions and DNA binding domains, and no potential interfering binding motifs were identified with the peptide chosen via a search performed using a publicly available protein family domain database and search program, Pfam (see, e.g., Bateman, et al. *Nucl Acids Res.* Database Issue 32:D138-D141, 2004).

2. Ease of peptide synthesis: Difficult residue patterns such as N-terminal Glu, multiple consecutive hydrophobic residues, and others are minimized.

3. Length: 12-20 amino acids is considered ideal.

4. Cross-reactivity: Peptide sequences are checked against protein databanks to minimize overlap with proteins other than the target protein. The search can be done with known search programs, e.g., BLAST. No significant overlap of the peptide with other human proteins was observed.

5. Conjugation requirements: An N-terminal or C-terminal cysteine is required for conjugation to carrier protein.

Bin1b transfection. The Bin1b gene was cloned to a PCMV-tab expression vector. T84 cells were seeded onto 35-mm plates at a density of $10^5$ per plate. The cells were grown to 60-80% confluency, transfected by using Lipofectin transfection reagent, and selected by using G418 (400 μg ml$^{-1}$) as described (Jiang et al., *J. Biol. Chem.* 276, 46870-46877(2001)).

Co-culture of sperm and epithelial cells. Immature caput sperm were collected from adult Sprague-Dawley rats (aged 3 months). The proximal caput epididymis was gently squeezed and punctured and then placed in 0.4 ml of warmed sperm medium (123 mM NaCl, 4 mM KCl, 2 mM CaCl$_2$, 0.4 mM MgSO$_4$, 0.3 mM Na, HPO$_4$, 25 mM NaHCO$_3$, 5 mM glucose, 12.5 mM sodium lactate and 0.5 mM pyruvate, 8 μg of phenol red, 4 mg ml$^{-1}$ bovine serum albumin; pH 7.4, osmolarity 310 mOsm kg$^{-1}$) in an incubator for 5 min to allow the sperm to disperse throughout the media. The sperm concentration was adjusted to $60 \times 10^6$ per ml. The methods for isolating and culturing epididymal epithelial cells have been described (Chan et al., *Exp. Physiol.* 81, 515-524 (1996)). On confluence (4 d after the start of culture), the culture medium in the apical compartment of cell culture was removed and replaced by 150 μl of fresh sperm medium 2 h before the coculture experiment. For coculture, we added 3 μl of sperm ($60 \times 10^6$ per ml) to the apical compartment of the cell culture and incubated the mixture for different durations at 37° C. and 5% CO$_2$. Aliquots of 10 μl were used for sperm motility analysis.

Sperm motility analysis. For the motility analysis, we used an HTM-IVOS system (version 10.8, Hamilton-Thorn Research) with the following settings: objective, ×4; minimum cell size, six pixels; minimum contrast, 65; minimum static contrast, 30; low VAP cut-off, 30.0; low VSL cut-off, 20.0; threshold straightness, 50%; static head size, 0.29-10.0; static head intensity, 0.29-1.11; magnification, 0.82. Sixty frames were acquired at a frame rate of 60 Hz. At least 200 tracks were measured for each specimen at 37° C. We recorded at least 30 points for each tract. The playback function of the system was used to check its accuracy.

Intracellular Ca$^{2+}$ concentration of caput epididymal sperm. Sperm were loaded with 2 μM Fura-2/AM for 45 min at 37° C. and 5% CO$_2$, washed twice and resuspended in sperm medium. The Fura-2-loaded sperm were then resuspended in different dilutions of conditioned medium from Bin-T84 cells or in conditioned medium from Vet-T84 cells as a control. The fluorescence signal from alternate excitation at 340 and 380 nm was recorded by a LS-50B luminescent spectrometer (Perkin Elmer), and the Ca$^{2+}$ concentration was calculated as described (Grynkiewicz et al., *J. Biol. Chem.* 260, 3440-3450 (1985)) using the 340/380 ratio of fluorescence.

Flow cytometry analysis. Rat sperm were stained with Bin1b polyclonal antibody at a final concentration of 1:200. In control samples, the antibody was replaced by preimmune serum at the same concentration. After incubation at 4° C. overnight, the sperm were washed twice with PBS containing 4 mg ml$^{-1}$ bovine serum albumin and incubated for 45 min at 22° C. with the secondary antibody, fluorescein isothiocyanate (FITC)-conjugated goat antibody against rabbit IgG (Zymed Laboratories) at a dilution of 1:50. After three washes, the sperm were analysed on a flow cytometer (Beckman Coulter). We analyzed 10,000 individual sperm per sample for FITC fluorescence emissions. A negative control of sperm stained by normal rabbit IgG was used to set the threshold for specific Bin1b staining. The percentage of sperm specifically stained for Bin1b was obtained by subtracting background fluorescence.

In vivo antisense oligonucleotide treatment. The skin covering the testis of a male Sprague-Dawley rat (aged >3 months) was cut open under anaesthesia and 30 μl of Bin1b antisense oligonucleotide (5'-AGAGTAACAAAACCTTCATG-3'; SEQ ID NO:3) or control sense oligonucleotide (5'-CATGAAGGTTTGTTACTCT-3'; SEQ ID NO:4) solution (20 μg ml$^-$) was injected into the proximal side of the mid-caput epididymis. The sperm were collected for assessment 48 h after injection. The use of animals in this project was authorized by the Animal Research Ethics Committee of The Chinese University of Hong Kong.

All patents, patent applications, and other publications cited in this application, including published amino acid or polynucleotide sequences, are incorporated by reference in the entirety for all purposes.

Sequence Listing

SEQ ID NO:1 (human EP2D amino acid sequence, GenBank Accession No. AAG21881 or NP_478108)

```
  1 mrqrllpsvt slllvallfp gssqarhvnh satealgelr erapgqgtng fqllrhavkr
 61 dllpprtppy qgdvppgirn ticrmqqgic rlffchsgek krdicsdpwn rccvsntdee
121 gkekpemdgr sgi
```

---

What is claimed is:

1. A method for evaluating fertility in a male suspecting of infertility, comprising the steps of:
   (a) obtaining a biological sample from the male, wherein the sample comprises sperm and at least some of the sperm are suspected of being bound by defensin EP2D, wherein said defensin EP2D is a polypeptide comprising the amino acid sequence of SEQ ID NO: 1;
   (b) determining the amount of defensin EP2D bound to the sperm; and
   (c) comparing the amount of defensin EP2D from step (b) with a standard control, wherein a decrease in the amount from the standard control indicates a decrease in fertility in the male.

2. The method of claim 1, wherein step (b) is performed by combining the sample with an antibody that specifically binds defensin EP2D under conditions permitting the binding between the antibody and defensin EP2D.

3. The method of claim 2, wherein the antibody is attached to a detectable label.

4. The method of claim 2, wherein step (b) is performed by flow cytometry.

5. The method of claim 2, wherein step (b) is performed by enzyme-linked imnmnosorbant assay (ELISA).

6. The method of claim 2, wherein step (b) is performed by western blot.

7. The method of claim 2, wherein step (b) is performed by immunostaining.

8. The method of claim 2, wherein step (b) is performed by determining the percentage of sperm bound by defensin EP2D.

9. The method of claim 2, wherein the sample and the antibody are further combined with a second antibody under conditions permitting the binding between the antibody and the second antibody, and wherein the second antibody is attached to a detectable label.

10. The method of claim 1, wherein step (b) is performed by enzyme-linked immunosorbant assay (ELISA).

* * * * *

SEQUENCE LISTING

<160> NUMBER OF SEQ ID NOS: 4

<210> SEQ ID NO 1
<211> LENGTH: 133
<212> TYPE: PRT
<213> ORGANISM: Homo sapiens
<220> FEATURE:
<223> OTHER INFORMATION: human epididymnis-specific beta-defensin EP2D;
      epididymis protein 2 (EP2); sperm associated
      antigen 11, isoform D precursor (SPAG11, SPAG11D);
      HE2beta1, epididymis-specific
<220> FEATURE:
<221> NAME/KEY: SIGNAL
<222> LOCATION: (1)..(25)
<223> OTHER INFORMATION: signal peptide
<220> FEATURE:
<221> NAME/KEY: PEPTIDE
<222> LOCATION: (26)..(133)
<223> OTHER INFORMATION: mature peptide

<400> SEQUENCE: 1

Met Arg Gln Arg Leu Leu Pro Ser Val Thr Ser Leu Leu Leu Val Ala
  1               5                  10                  15

Leu Leu Phe Pro Gly Ser Ser Gln Ala Arg His Val Asn His Ser Ala
                 20                  25                  30

Thr Glu Ala Leu Gly Glu Leu Arg Glu Arg Ala Pro Gly Gln Gly Thr
             35                  40                  45

Asn Gly Phe Gln Leu Leu Arg His Ala Val Lys Arg Asp Leu Leu Pro
     50                  55                  60

Pro Arg Thr Pro Pro Tyr Gln Gly Asp Val Pro Pro Gly Ile Arg Asn
 65                  70                  75                  80

Thr Ile Cys Arg Met Gln Gln Gly Ile Cys Arg Leu Phe Phe Cys His
                 85                  90                  95

Ser Gly Glu Lys Lys Arg Asp Ile Cys Ser Asp Pro Trp Asn Arg Cys
                100                 105                 110

Cys Val Ser Asn Thr Asp Glu Glu Gly Lys Glu Lys Pro Glu Met Asp
            115                 120                 125

Gly Arg Ser Gly Ile
        130

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:EP2D peptide
      for immunogen, 16mer peptide C113-D128

<400> SEQUENCE: 2

Cys Val Ser Asn Thr Asp Glu Glu Gly Lys Glu Lys Pro Glu Met Asp
  1               5                  10                  15

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:human EP2D
      peptide orthologue rat Bin1b antisense
      oligonucleotide

<400> SEQUENCE: 3
agagtaacaa aaccttcatg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:control
      sense oligonucleotide

<400> SEQUENCE: 4
catgaaggtt ttgttactct                                              20
```